US008483817B2

(12) United States Patent
Björling

(10) Patent No.: US 8,483,817 B2
(45) Date of Patent: Jul. 9, 2013

(54) METHOD AND IMPLANTABLE MEDICAL DEVICE FOR ASSESSING A DEGREE OF PULMONARY EDEMA OF A PATIENT

(75) Inventor: Anders Björling, Solna (SE)

(73) Assignee: St. Jude Medical, AB, Jarfalla (SE)

( * ) Notice: Subject to any disclaimer, the term of this patent is extended or adjusted under 35 U.S.C. 154(b) by 1011 days.

(21) Appl. No.: 12/282,912

(22) PCT Filed: Mar. 15, 2006

(86) PCT No.: PCT/SE2006/000338
§ 371 (c)(1),
(2), (4) Date: Sep. 15, 2008

(87) PCT Pub. No.: WO2007/105996
PCT Pub. Date: Sep. 20, 2007

(65) Prior Publication Data
US 2009/0099475 A1    Apr. 16, 2009

(51) Int. Cl.
*A61B 5/05* (2006.01)
(52) U.S. Cl.
USPC .......................................... 600/547; 600/595
(58) Field of Classification Search
USPC .................................................. 600/547, 595
See application file for complete search history.

(56) References Cited

U.S. PATENT DOCUMENTS

| 5,562,711 | A | 10/1996 | Yerich et al. |
| 6,473,640 | B1 * | 10/2002 | Erlebacher ..................... 600/547 |
| 6,490,485 | B1 * | 12/2002 | Sun et al. ......................... 607/20 |
| 6,512,949 | B1 | 1/2003 | Combs et al. |
| 6,595,927 | B2 | 7/2003 | Pitts-Crick et al. |
| 2004/0102712 | A1 | 5/2004 | Belalcazar et al. |
| 2005/0216067 | A1 | 9/2005 | Min et al. |
| 2005/0288726 | A1 * | 12/2005 | Gollasch et al. ................ 607/17 |

FOREIGN PATENT DOCUMENTS

| EP | 0985429 | * | 9/1999 |
| EP | 0 985 429 A2 | | 3/2000 |
| EP | 1 598 093 A2 | | 11/2005 |
| WO | WO 98/33554 A1 | | 8/1998 |
| WO | WO 2006/068566 A1 | | 6/2006 |

OTHER PUBLICATIONS

"Evaluation of Transthoracic Electrical Impedance in the Diagnosis of Pulmonary Edema," Fein et al., Circulation, vol. 60, No. 5, (1979) pp. 1156-1160.

* cited by examiner

*Primary Examiner* — Max Hindenburg
*Assistant Examiner* — Renee Danega

(57) ABSTRACT

In a method and an implantable medical device for assessing a degree of pulmonary edema of a patient, at least two specific body patients of the patent are detected and at least one impedance sensing session is initiated to sense trans-thoracic impedance signals from the patient when the patient is in one of the at least two specific positions. Impedance values are obtained from the impedance signals, and a relation between respective impedance values at the at least two positions is determined. This relation is then used as a metric of pulmonary edema to assess the degree of pulmonary edema, and is provided as an output.

34 Claims, 3 Drawing Sheets

METHOD AND IMPLANTABLE MEDICAL DEVICE FOR ASSESSING A DEGREE OF PULMONARY EDEMA OF A PATIENT

BACKGROUND OF THE INVENTION

1. Field of the Invention

The present invention generally relates to implantable medical devices, such as cardiac pacemakers and implantable cardioverter/defibrillators, and in particular to an improved method and an implantable medical device for assessing a degree of pulmonary edema of a patient.

2. Description of the Prior Art

Today, in the modern society, heart diseases and/or conditions leading to an impaired heart function are a major problem entailing constantly increasing costs for medical services. For example, heart failure is a condition which affects thousands of people throughout the world. Congestive heart failure (CHF) is the inability of the heart to supply the body with an adequate amount of blood. Patients suffering from CHF are often afflicted by cardiogenic pulmonary edema, which is caused by the accumulation of fluid in the lung interstitium and alveoli due to the fact the left ventricular venous return exceeds left ventricular cardiac output. That is, more fluids are transported to the lung region than from the lung region causing the accumulation of fluids in the lung region. Hence, pulmonary edema is a common effect of congestive heart failure (CHF) and CHF patients are often on diuretics to decrease the risk of this. However, diuretics can be difficult to titrate and the amount needed may differ from day to day. Accordingly, reliable and accurate information that can be used to assess a degree of pulmonary edema or amount of pulmonary fluid would be of great use. Such information should also be easy and convenient to obtain, should be sensitive to early changes of the pulmonary fluid, and should be obtained automatically. In this respect, the electrical bio-impedance and, in particular, the trans-thoracic impedance have been found to constitute an effective measure for identifying changes of different conditions of the body of a patient, such as incipient pulmonary edema and the progression of pulmonary edema due to CHF, i.e. the accumulation of fluids in the lung-region associated with pulmonary edema affects the thoracic impedance, or more specifically the DC impedance level, since the resistivity of the lung changes in accordance with a change of the ratio of fluid to air. The DC impedance level is negatively correlated with the amount of fluids in the lung. Studies have shown that hospitalization due to the development of acute CHF with the symptom pulmonary edema was preceded two or three weeks by a drop in the DC impedance by approximately 10-15%.

In light of this, many approaches have been suggested for providing information that can be used to assess a degree of pulmonary edema or amount of pulmonary fluid by utilizing the thoracic impedance. In U.S. Pat. No. 6,595,927 a method and system for diagnosing pulmonary congestion in a mammalian heart using trans-thoracic impedance is disclosed. The trans-thoracic impedance and a heart rate of a patient are measured and an activity sensor is used to sense a heart activity in order to determine an exercise level of the patient. The impedance change over time intervals between commencement and termination of exercise is used as a quantitative measure of the degree of pulmonary congestion. Another approach is shown in U.S. Pat. No. 6,104,949, where a method and system for diagnosing pulmonary congestion in a mammalian heart using trans-thoracic impedance is disclosed. The trans-thoracic impedance is measured and a body posture of the patient is sensed. Changes in posture is correlated with trans-thoracic impedance changes and the impedance change over a time interval after a posture change is used as a quantitative measure of the degree of congestive heart failure.

However, a problem associated with present methods for measuring the electrical bio-impedance and, in particular, the trans-thoracic impedance is the accurateness and reliability of the obtained signals since they are greatly affected by factors like the body position of the patient, patient activity levels, heart rate frequency, etc. For example, it has been found that the body position of the patient is of major importance with regard to the thoracic impedance. In addition, it has recently been found that the posture or position dependence also is of a significant magnitude regarding different positions even when the patient is lying down, for example, whether the patient is lying on a side or is lying on the back. A major reason is that an impedance measurement depends on the measurement vector, i.e. the vector between the nodes that the current is applied between and the vector the voltage is measured between. When the body shifts position, these vectors will change since the gravity will influence, for example, tissue between the nodes and how it moves. Tests performed on animals have shown that the trans-thoracic impedance may vary up to 20% depending on the position of the animal.

Accordingly, there is a need for an improved method and implantable medical device for assessing a degree of pulmonary edema of a patient or for obtaining reliable and accurate information for such an assessment in an automatic way.

SUMMARY OF THE INVENTION

Thus, an object of the present invention is to provide an improved method and implantable medical device for assessing a degree of pulmonary edema of a patient.

Another object of the present invention is to provide an improved method and implantable medical device for obtaining reliable and accurate information for use in assessments of a degree of pulmonary edema of a patient.

A further object of the present invention is to provide an improved method and implantable medical device for automatically assessing a degree of pulmonary edema of a patient and for obtaining reliable and accurate information for such an assessment in an automatic way.

In the context of this application, the term "impedance" refers to both the DC component and the AC component of the impedance if not otherwise stated. The impedance is calculated as $z=u/i$, where u is the measured voltage between two electrodes and i is the applied excitation current between the two electrodes. As indicated above, the measured impedance consists of a DC component and an AC component, where the DC component is the baseline around which the AC component fluctuates. The DC component reflects the amount of tissue and fluids that are located between the measuring points that the impedance is measured in-between and the AC components reflects how, for example, respiration and cardiac activity influence the impedance signal.

For clarity, the term "trans-thoracic impedance" refers to an impedance measured over the thorax of the patient. For example the excitation current may be applied between an RV-tip (i.e. distal electrode in a bipolar lead located in right ventricle) and the case (or housing), and the voltage may be measured between the case and an RV-ring (i.e. the proximal electrode in a bipolar lead located in right ventricle).

According to an aspect of the present invention, a method for assessing a degree of pulmonary edema of a patient using an implantable medical device includes detecting at least two specific body positions of the patient; initiating at least one impedance sensing session to sense trans-thoracic impedance signals when the patient is in one position of the at least two specific positions; obtaining impedance values from the impedance signals; determining a relation between respective impedance values at the at least two positions; storing the relation; and using the relation as a metric of pulmonary edema to assess the degree of pulmonary edema.

According to a second aspect of the present invention, an implantable medical device for assessing a degree of pulmonary edema of a patient is connectable to the patient in at least one electrode configuration. The device has an impedance sensor adapted to sense a trans-thoracic impedance of the patient via the at least one electrode configuration; position information obtaining circuit adapted to obtain information related to body positions of the patient; obtaining means adapted to obtain impedance values from the impedance signals; a processing unit adapted to: determine whether the patient is in one of at least two specific body positions using the position information; trigger the impedance sensor to initiate a sensing session in order to sense a trans-thoracic impedance when the patient is in one position of the at least two specific positions; and determine a relation between respective impedance values at the at least two positions; a storage adapted to store the relation; and wherein the relation is used as a metric of pulmonary edema to assess the degree of pulmonary edema:

According to a further aspect of the present invention, a computer readable medium is encoded with programming instructions that cause a computer to perform a method according to the first aspect of the present invention.

As discussed above, the body posture has been shown to heavily influence the impedance level, i.e. the DC level, since the fluid moves around in the body as the body posture is changed. The present invention does, however, in fact utilize this phenomenon, i.e. that the DC impedance level varies with posture, to obtain a measure of the amount fluid. To elaborate, a relation between impedance values obtained for at least two body positions is used as a metric of pulmonary edema to assess the degree of pulmonary edema. This is based on the assumption that if there is a high amount of fluid, the DC impedance level will behave in a different manner when the patient changes his or hers posture in comparison to the DC impedance level of patient having a smaller amount of fluid. This is due to the fact that the more fluid that is present in thorax, the more fluid will move around when the patient changes his or her posture.

In one embodiment of the present invention, the variability of the impedance values between different body positions is determined. In this embodiment, the assumption is that the more fluid that is present in thorax, the more fluid will move around when the patient changes his or hers posture and, hence the more variability will be found in the DC impedance signal.

In one embodiment the impedance values are transferred to an external unit, for example, a programming unit via a communication link, for example, a telemetry link. The relation between respective impedance values at the at least two positions is determined and used as a metric of pulmonary edema to assess the degree of pulmonary edema by the programming unit.

According to an embodiment of the present invention, an activity level signal of the patient is sensed and the sensed activity level signal is used to detect the body positions of the patient.

In another embodiment of the present invention, when one of the at least two specific body positions is sensed, the initiating of the impedance sensing session is delayed a predetermined period of time. Thereby, the performance and accuracy of the impedance measurements can be improved since the condition during which the measurements are performed has stabilized after a positions change. This is due to the fact that it takes some time for the interstitial and/or pulmonary fluid to redistribute in the body.

According to a further embodiment of the present invention, it is checked whether the sensed activity level signal is below a predetermined activity level signal limit; and it is detected that the patient is lying down when the sensed activity level signal has been below the signal limit during a predetermined period of time.

In a further embodiment of the present invention, an AC impedance morphology is created using the AC impedance values of the impedance signals; and it is detected whether the patient is lying on the back, the stomach, or on a side using the AC impedance morphology. Other measures such as heart rate, rate of breathing, size of breath can also be used to further improve the ability to accurately identify a specific body posture. Moreover, blood pressure and/or blood flow may also be used to improve the ability to accurately identify a specific body posture.

In alternative embodiments of the present invention, a morphology of the sensed activity level signal is determined; the sensed morphology is compared with a reference morphology; and it is detected that the patient is walking if the sensed morphology and the reference morphology shows a correspondence within predetermined terms of reference. In an alternative embodiment, a frequency of the sensed activity level signal is determined; the sensed frequency is compared with a reference frequency; and it is detected that the patient is walking if a difference between the sensed frequency and the reference frequency is determined to be within a predetermined frequency range. The reference morphology and/or the reference frequency may be pre-stored in the medical device.

In one embodiment, the reference morphology and/or the reference frequency are obtained during a training session or initialization procedure, which may be performed at a follow-up visit after the implantation. The initialization protocol is initiated using an external programmer and the patient is asked to walk normally in the room for a while. The device stores the specific features of walking for that particular patient, including the frequency and signal morphology of the activity signal. Hence, the sensed morphology and/or frequency of the sensed activity level signal when the patient is walking is stored as a reference morphology and/or a reference frequency. The session includes the steps of determining a morphology and/or frequency of a sensed activity level signal when the patient is walking; and storing the determined morphology and/or frequency of the sensed activity level signal when the patient is walking as a reference morphology and/or a reference frequency, respectively.

In one embodiment, an excitation current pulse is applied between a first electrode, for example, arranged to be positioned within the heart of the patient and a second electrode, for example, the case of the device and the voltage between the first and second electrode resulting from the excitation current pulse is sensed. As an example, the excitation current may be applied between the case (or housing) and an RV-tip (i.e. distal electrode in a bipolar lead located in right ventricle), and the voltage may be sensed between the case and an RV-ring (i.e. .e. the proximal electrode in a bipolar lead located in right ventricle). According to another example, the excitation current is to be applied between the case and an RA-tip (i.e. the distal electrode in a bipolar lead located in right atrium) and the voltage is sensed between the case and RA-ring (i.e. the proximal electrode in a bipolar lead located in right atrium). Those skilled in the art will realize there are other conceivable configurations that can be used. According to one embodiment, the first and second electrodes are arranged in a lead connectable to the device and arranged to be located in a right ventricle, in a right atrium, or in a left ventricle of the patient.

In yet another embodiment of the present invention, three specific body positions are detected, a derivative of the impedance values is calculated with respect to body position; and the derivative is used to assess the degree of pulmonary edema.

The assessed degree of pulmonary edema may be used to determine a suitable titration of a dose of diuretics to be delivered to the patient.

Furthermore, the assessed degree of pulmonary edema may be used to diagnose congestive heart failure.

In one embodiment, each impedance value is calculated as a mean value of impedance values obtained during a predetermined period of time; and a relation between respective impedance values at the at least two positions is determined using the calculated impedance values. Thereby, the accuracy and reliability of the impedance values can be increased and thus, in turn, the accuracy and reliability of relation between respective impedance values may be improved.

Alternatively, each relation between impedance values obtained in the at least two specific positions may be calculated as a mean value of relations obtained during a predetermined period of time.

As those skilled in the art will appreciate, the methods of the present invention, as well as preferred embodiments thereof, are suitable to be performed by the operation of a computer program or a computer readable medium.

The features that characterize the invention, both as to organization and to method of operation, together with further objects and advantages thereof, will be better understood from the following description used in conjunction with the accompanying drawings. It is understood that the drawings are for the purpose of illustration and description and is not intended as a definition of the limits of the invention. These and other objects attained, and advantages offered, by the present invention will become more fully apparent as the description that now follows is read in conjunction with the accompanying drawings.

DESCRIPTION OF THE PREFERRED EMBODIMENTS

Figure 1:
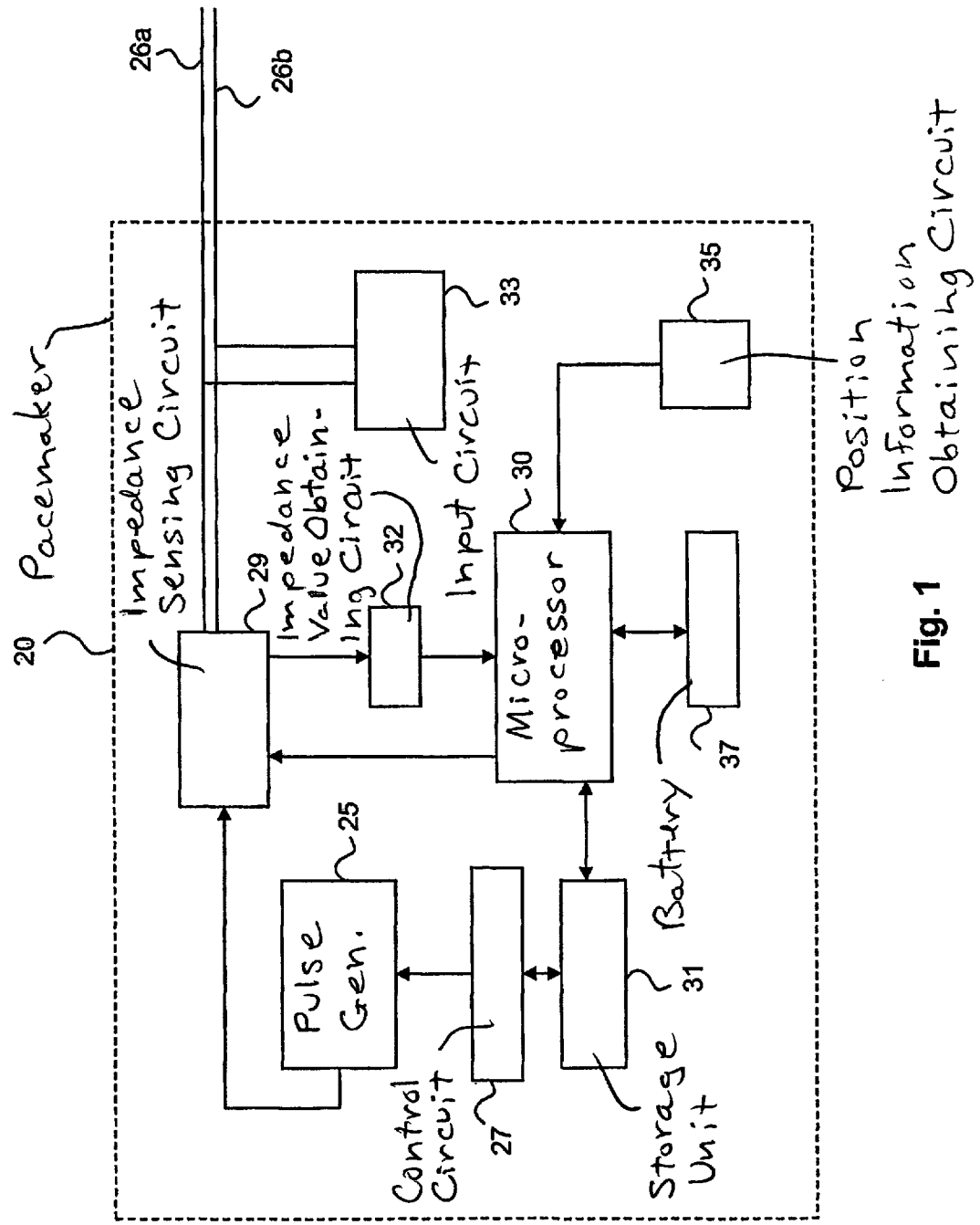
FIG. 1 is block diagram of the primary functional components of a first embodiment of an implantable medical device in accordance with the present invention.

With reference first to FIG. 1, the configuration including the primary functional components of a first embodiment of an implantable medical device in accordance with the present invention will be described. In the following, the present invention will be described in the context of a pacemaker. However, as the person skilled within the art easily realizes, the present invention may also be implemented within the contents of, for example, an implantable cardioverter/defibrillator.

The illustrated embodiment shows an implantable medical device, such as a pacemaker. The pacemaker 20 has a housing that is hermetically sealed and biologically inert. Normally, the housing is conductive and may, thus, serve as an electrode. One or more pacemaker leads, where only two are shown in FIG. 1, namely a ventricular lead 26a and an atrial lead 26b, are electrically coupled to the pacemaker 20 in a conventional manner. The leads 26a, 26b extend into the heart (not shown) via a vein of the patient. One or more conductive electrodes for receiving electrical cardiac signals and/or for delivering electrical pacing to the heart may be arranged near the distal ends of the leads 26a, 26b. As the skilled man in the art realizes, the leads may be implanted with its distal end located in either the atrium or ventricle of the heart.

The leads 26a, 26b may be unipolar or bipolar, and may include any of the passive or active fixation means known in the art for fixation of the lead to the cardiac tissue. As an example, the lead distal tip (not shown) may include a tined tip or a fixation helix. The leads 26a, 26b carry one or more electrodes, such a tip electrode or a ring electrode, arranged to, inter alia, transmit pacing pulses for causing depolarization of cardiac tissue adjacent to the electrode(-s) generated by a pace pulse generator 25 under influence of a control circuit 27. The control circuit 27 controls pace pulse parameters such as output voltage and pulse duration.

Moreover, an impedance sensing circuit 29 is adapted to sense impedance signals. In one embodiment, the impedance sensing circuit 29 is adapted to carry out impedance measurements for sensing a trans-thoracic impedance. The impedance sensing circuit 29 is arranged to apply excitation current pulses between a first electrode and second electrode adapted to positioned, for example, within a heart of the patient in an embodiment where the cardiogenic impedance is measured. The impedance sensing circuit 29 is also arranged to sense the impedance in the tissues between the first and second electrode to the excitation current pulse. Further, the impedance sensing circuit 29 is coupled to a processing unit, for example, a microprocessor 30, where, inter alia, processing of the obtained impedance signals can be performed. In an embodiment where the trans-thoracic component of the electrical bio-impedance is sensed, the impedance circuit 29 is arranged to apply an excitation current pulse between a first electrode, for example, arranged to positioned within the heart of the patient and a second electrode, for example, the case of the device and to sense the voltage between the first and second electrode resulting from the excitation current pulse. As an example, the excitation current may be applied between the case (or housing) and an RV-tip (i.e. distal electrode in a bipolar lead located in right ventricle), and the voltage may be sensed between the case and an RV-ring (i.e. .e. the proximal electrode in a bipolar lead located in right ventricle). According to another example, the excitation current is being applied between the case and an RA-tip (i.e. the distal electrode in a bipolar lead located in right atrium) and the voltage is sensed between the case and the RA-ring (i.e. the proximal electrode in a bipolar lead located in right atrium). Of course, as the skilled man realizes, there are other conceivable configurations that can be used.

According to this embodiment, the impedance sensor 29 is connected to a value obtaining circuit 32 adapted to obtain the DC component of the impedance signals. According to one embodiment, the value obtaining circuit is a low pass filter having a limiting frequency of 0.2 Hz. The impedance sensing circuit 29 is controlled by the microprocessor 30 and the control circuit 27. The control circuit 27 acts under the influence of the microprocessor 30. A storage unit 31 is connected to the control circuit 27 and the microprocessor 30, which storage unit 31 may include a random access memory (RAM) and/or a non-volatile memory such as a read-only memory (ROM). Detected signals from the patient's heart are processed in an input circuit 33 and are forwarded to the microprocessor 30 for use in logic timing determination in known manner. For example, the input circuit 33 is connected to cardiogenic sensors located in the lead 26a and/or 26b adapted to sense events of the heart cycles of the patient, such as a P-wave, a R-wave in the right or left ventricle or a pacing pulse in one of the heart chambers.

The implantable medical device 20 is powered by a battery 37, which supplies electrical power to all electrical active components of the medical device 20. Data contained in the storage unit 31 can be transferred to a programmer (not shown) via a programmer interface (not shown). The implantable medical device 20 according to the present invention further comprises a position information obtaining circuit 35 adapted to obtain information related to body positions of the patient. The position information obtaining circuit 35 is connected to the microprocessor 30. The microprocessor 30 is adapted to determine which position the patient is in of at least two specific predetermined body positions or postures using the position information from the position information obtaining circuit 35. In one embodiment, the microprocessor 30 is adapted to send a triggering signal to the impedance sensor 29 to initiate a sensing session in order to sense a trans-thoracic impedance when the patient is in either one of the at least one position. In one embodiment, the initiating of the impedance sensing session is delayed a predetermined period of time thereby allowing the interstitial and/or pulmonary fluid to redistribute in the body after a change of body position. This predetermined period of time may be programmed into the device. In other embodiments, the implantable medical device may also include other sensors such as a heart rate sensor adapted to sense a heart rate of the patient, or a breath rate sensor adapted to sense a breath rate of the patient and/or a breath size of the patient. The information obtained by means of these sensors may be used to further increase the accuracy and reliability in the position determination.

The microprocessor 30 is adapted to determine a relation between respective impedance values obtained at the at least two positions, which may be stored in the storage unit 31. The relations may be used as a metric of pulmonary edema to assess the degree of pulmonary edema. In one embodiment, the variability of the impedance values between different body positions is determined. The assumption is accordingly that the more fluid that is present in thorax, the more fluid will move around when the patient changes his or hers posture and, hence the more variability will be found in the DC impedance signal is utilized. This is shown schematically in FIG. 2 where the DC impedance variation with posture for two different subjects with a different degree of fluid in the thorax is shown. The DC impedance at different postures, i.e. supine and upright, for a subject having high amount of fluid is indicated by the unbroken line and the DC impedance at the same postures for a subject having low amount of fluid is indicated by the broken line.

In an alternative embodiment, the impedance values at the different positions and/or the relations can be transferred to an external programmer (not shown). In this case, the signals and/or relations are transferred to the external programmer from the implantable medical device via a telemetry link (not shown)

According to one embodiment, the position information obtaining circuit 35 is an activity level sensor connected to the microprocessor 30 adapted to sense an activity level of the patient supply the microprocessor 30 with an activity level signal. The microprocessor 30 may be adapted to determine whether the sensed activity level signal is below a predetermined activity level signal limit and determine that the patient is lying down if the sensed activity level signal is found to be below the signal limit during a predetermined period of time. Thus, a low activity level during a long period of time, i.e. the patient is inactive, is a significant indication of that the patient is sleeping and, moreover, that he or she is lying down. However, in order to improve the accuracy and reliability of the method it may also be advantageous to identify whether the patient is lying, for example, on the back, on the stomach, or on a side. As discussed above, it has been found that the posture or position dependence also is of a significant magnitude regarding different positions when the patient is lying down, for example, whether the patient is lying on the back, on the stomach, or on a side. A major reason is that an impedance measurement depends on the measurement vector, i.e. the vector between the nodes that the current is applied between and the vector the voltage is measured between. When the body shifts position, these vectors will change since the gravity will influence, for example, tissue between the nodes and how it moves. Tests performed on animals have shown that the trams-thoracic impedance may vary up to 20% depending on which position the animal was lying in. In order to identify whether the patient is lying on the back, on the stomach, or on a side, the AC impedance components of the impedance signals are taken care of in the low pass filter 32, i.e. the signal components above the limit frequency of 0.2 Hz. The AC components of the signals is analyzed in the microprocessor 30 and the fact that the impedance morphology is very posture dependent is utilized to determine whether the patient is lying on the back, on the stomach, or on a side.

Furthermore, the microprocessor 30 is adapted to determine a morphology of the sensed activity level signal and the sensed morphology with a reference morphology is compared with a reference morphology, which may be pre-stored in the storage 31. It is determined that the patient is walking if the sensed morphology and the reference morphology show a correspondence within predetermined terms of reference. Alternatively, a frequency of the sensed activity level signal may be determined and compared with a reference frequency. In this case, it is detected that the patient is walking if a difference between the sensed frequency and the reference frequency is determined to be within a predetermined frequency range. According to another embodiment, both the morphology and the frequency of the sensed activity level signal are used to identify if the patient is walking. The reference morphology and/or the reference frequency may be pre-stored in hardware (e.g. in the storage) or software (e.g. implemented in the processing unit) of the implantable medical device.

According to another embodiment, the reference morphology and/or the reference frequency are obtained during a training session or initialization procedure, which may be performed at a follow-up visit after the implantation. The initialization protocol is initiated using an external programmer and the patient is asked to walk normally in the room for a while. The device stores the specific features of walking for that particular patient, including the frequency and signal morphology of the activity signal. Hence, the sensed morphology and/or frequency of the sensed activity level signal when the patient is walking is stored as a reference morphology and/or a reference frequency.

In one embodiment of the present invention, the position information obtaining circuit 35 is a position sensor adapted to detect the position or posture of the patient. The position sensor may be, for example, a 3 axis accelerometer. The position sensor can be incorporated in the device in accordance with conventional practice within the art.

Figure 3:
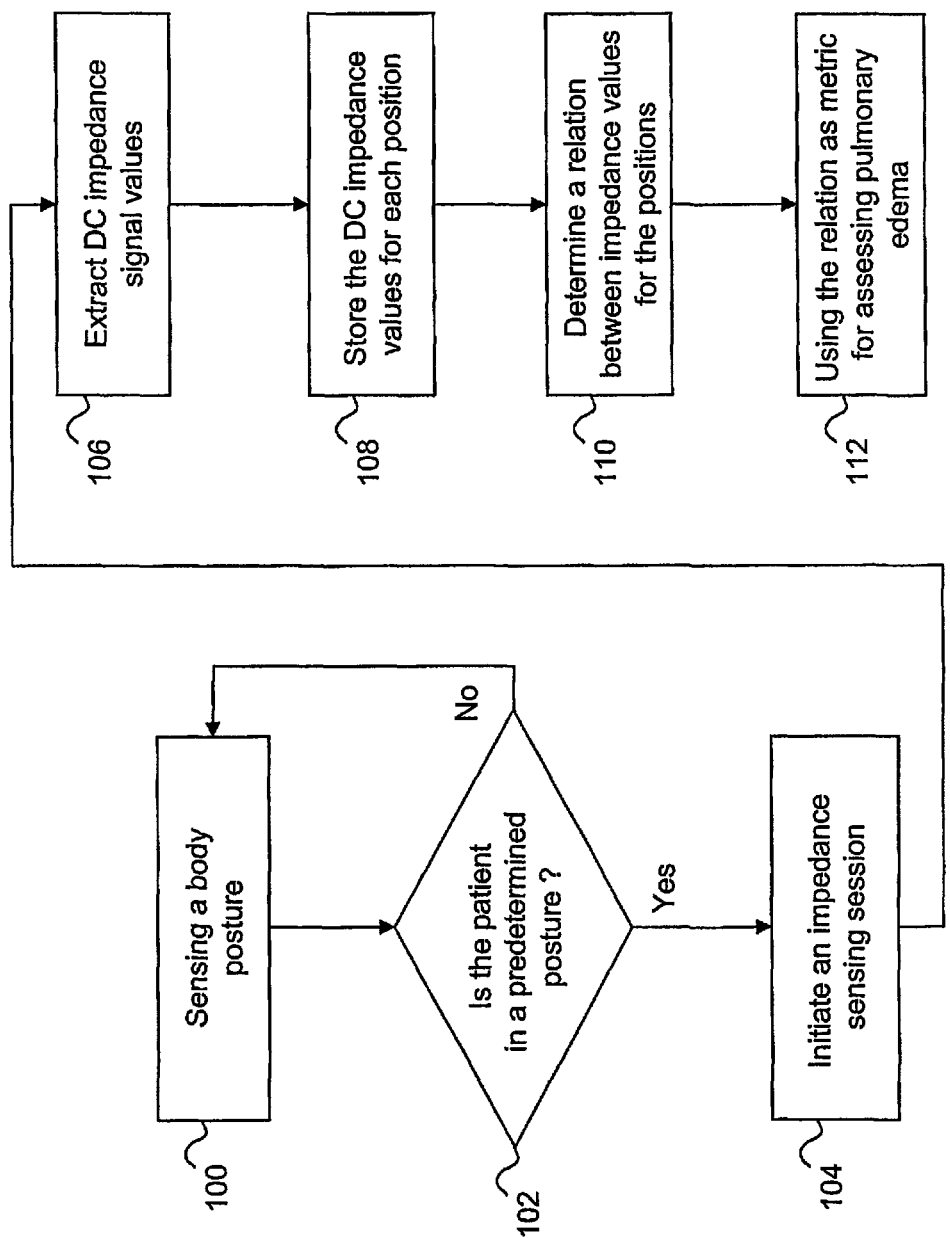
FIG. 3 is a high-level description of the method for assessing a degree of pulmonary edema of a patient using an implantable medical device according to the present invention.

Referring now to FIG. 3, a detailed description of the method for assessing a degree of pulmonary edema of a patient using an implantable medical device according to the present invention will be given. First, in step 100, the body position or posture of the patient is sensed or, in other words, position information is obtained. This may be performed by means of the activity level sensor 35. Then, in step 102, the microprocessor 30 identifies or determines whether the patient is in one of at least two predetermined postures using the position information. In one embodiment, these predetermined postures are when the patient is lying and when the patient is walking, which can be identified in accordance with the description above. In one embodiment, if it has been determined that the patient is lying down, a further determination may be executed in order to identify whether the patient is lying on the back, on the stomach, or on a side. In this case, the AC impedance components of the impedance signals are obtained from filter 32, i.e. the signal components above the limit frequency of 0.2 Hz, and analysed in the microprocessor 30 and the fact that the impedance morphology is very posture dependent is utilized to determine whether the patient is lying on the back, on the stomach, or on a side. In accordance to other embodiments, other information such as heart rate, rate of breathing, and/or size of breath can be obtained and used in the determination of the position to further improve the ability to accurately identify a specific body posture.

If it is determined that the patient is not in any one of the predetermined positions, the procedure returns to step 100. However, if it is determined the patient is in one of the predetermined positions, the procedure proceeds to step 104 where an impedance sensing session to obtain impedance signals is initiated. According to an embodiment, the initiating of the impedance sensing session is delayed a predetermined period of time. Thereby, accuracy and reliability of the sensed signals may be improved due to the fact that it takes some time for the interstitial and/or pulmonary fluid to redistribute in the body after a change of body position. In yet another embodiment, information regarding heart rate, rate of breathing, a blood flow, a blood pressure, or size of breath is obtained and used to further improve the accuracy in the impedance measurements. For example, it may be determined that the impedance sensing session only is initiated if the heart rate of the patient is within a predetermined interval or if the rate of breathing is in a predetermined interval.

Figure 2:
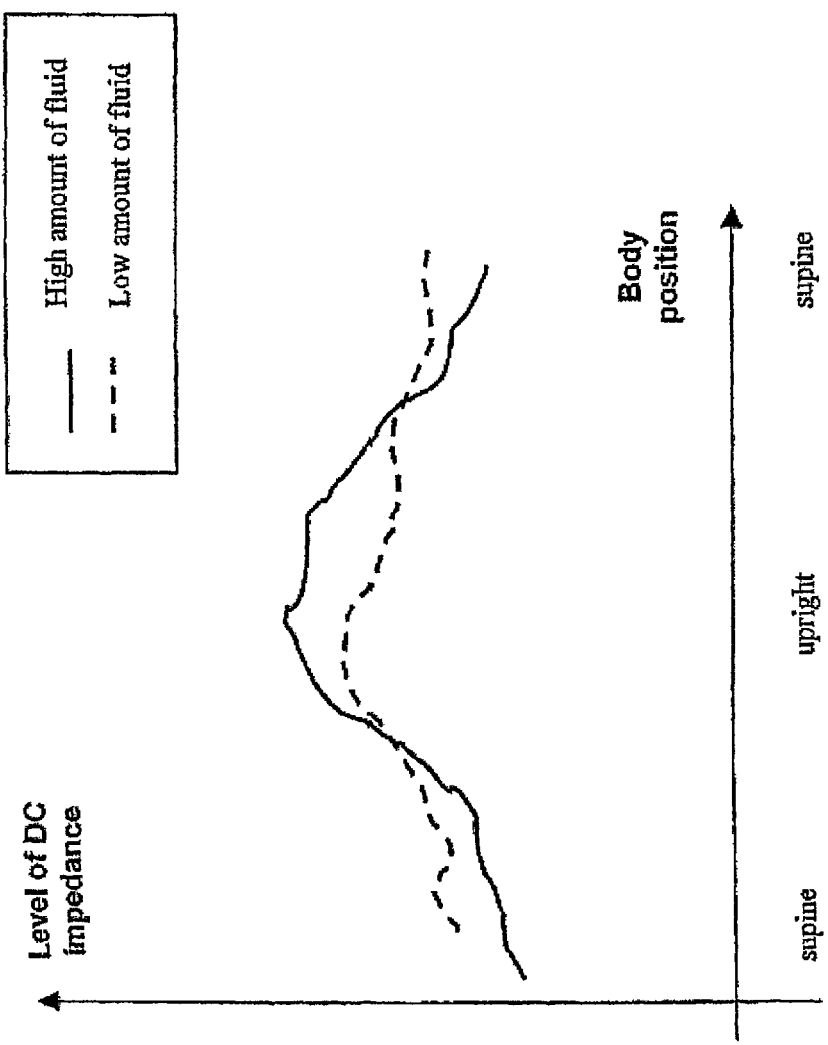
FIG. 2 is a schematic diagram showing the DC impedance variation with posture for two different subjects with a different degree of fluid in the thorax.

Thereafter, at step 106, impedance values are obtained from the sensed impedance signals. In one embodiment, the AC impedance component of the signal is filtered off in the low pass filter 32 (i.e., the signal components above the limit frequency of 0.2 Hz is filtered off). The remaining DC component (i.e. the signal components below the limit frequency of 0.2 Hz) is the supplied to the microprocessor 30. Then, at step 108, the obtained DC component is stored, for example, in the storage unit 31. At step 110, a relation between respective impedance values for the two positions is determined and stored. In one embodiment, the variability of the impedance values between different body positions is determined. In FIG. 2 the DC impedance variation with posture for two different subjects with a different degree of fluid in the thorax is shown. The DC impedance at different postures, i.e. supine and upright, for a subject having high amount of fluid is indicated by the unbroken line and the DC impedance at the same postures for a subject having low amount of fluid is indicated by the broken line. In one embodiment, it is checked whether a predetermined number of DC impedance values has been obtained for each position and a means value for each position is calculated. Alternatively, a weighted average value may be calculated for each position using the predetermined number of values. Subsequently, at step 112, the relation(-s) is (are) used as a metric or measure of pulmonary edema to assess the degree of pulmonary edema. A measure based on the derivative of the DC component with respect to body posture may be the difference between the average DC impedance between two positions. If one value per day and per position are created, the variability measure would be the difference between the two values. Thus, one single value in Ohms per day would be trended.

In another embodiment, the DC impedance value for each body posture is an average of a number of measurements and the difference in impedance is divided with the standard deviation of these values.

If more than two body postures are used, the difference between all pairs of body postures may be added. Thus, the value to trend would be $$|v1-v2|+|v2-v3|+|v1-v3| \qquad (1)$$

where vX is the DC impedance at body posture X. If the differences are divided with the standard deviation, the value to trend would be $$(|v1-v2|)/s12+(|v2-v3|)/s23+(|v1-v3|)/s13 \qquad (2)$$

where sXY is the composite standard deviation for values at postures X and Y.

The values obtained in accordance with (1) or (2) may hence be used to trend the pulmonary edema. For example, a current relation may be compared with at least one preceding relation to determine a difference between the current relation and the at least one preceding relation. Thereby, it is possible to identify trends in the impedance such as long-term changes in the impedance, which can be used to assess the degree of pulmonary edema. This, can, in turn, be used to detect, for example, CHF. The relation or trend values can also be compared with at least one reference relation value to determine a difference between the current relation and the at least one reference relation, which also may be used to identify trends in the impedance such as long-term changes in the impedance in order to assess the degree of pulmonary edema.

These calculations may be performed in the medical device or, in an alternative embodiment, the impedance values at the different positions and/or the relations can be transferred to an external programmer for executing of the calculations. In this case, the signals and/or relations are transferred to the external programmer from the implantable medical device via a telemetry link.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

The invention claimed is:

1. A method for assessing a degree of pulmonary edema of a patient using an implantable medical device, comprising the steps of:

detecting first, second and third different body positions of said patient, the first body position being an upright position and the second body position and the third body position being a respective one of lying on the back, on the stomach, or on a side, wherein the step of detecting first, second, and third different body positions comprises the steps of:

sensing an activity level signal of said patient;

using said sensed activity level signal to detect said body positions of said patient;

determining whether said sensed activity level signal is below a predetermined activity level signal limit; and detecting that the patient is lying down when said sensed activity level signal has been below said signal limit during a predetermined period of time;

sensing first trans-thoracic impedance signals when said patient is in the first position, sensing second thoracic impedance signals when said patient is in the second position, and sensing third trans-thoracic impedance signals when said patient is in the third position;

obtaining first, second, and third impedance values respectively from said first, second, and third impedance signals;

determining a relation among the respective first, second, and third impedance values;

storing said relation; and using said relation as a metric of pulmonary edema to assess the degree of pulmonary edema;

wherein the step of detecting that the patient is lying down when said sensed activity level signal has been below said signal limit during a predetermined period of time comprises the steps of:

obtaining AC impedance values from said impedance signals;

creating an AC impedance morphology using said AC impedance values; and detecting whether the patient is lying on the back, on the stomach, or on a side using an AC impedance morphology.

2. The method according to claim 1, wherein the step of determining a relation comprises the step of:

determining the variability of the first and second impedance values, as said relation.

3. The method according to claim 1, further comprising the steps of:

comparing a current relation with at least one preceding relation to determine a difference between said current relation and said at least one preceding relation; and using said difference to assess the degree of pulmonary edema.

4. The method according to claim 1, wherein the step of using said relation comprises the steps of comparing a current relation with at least one reference relation value to determine a difference between said current relation and said at least one reference relation; and using said difference to assess the degree of pulmonary edema.

5. The method according to claim 1, wherein the step of obtaining comprises:

filtering said impedance signals in order to obtain DC impedance values.

6. The method according to claim 1, wherein the step of detecting at least two specific positions further comprises:

when one of said first, second or third body positions is sensed, delaying the initiating of the impedance sensing session a predetermined period of time sufficient to allow the interstitial and/or pulmonary fluid to redistribute in the body.

7. The method according to claim 1, further comprising the steps of:

sensing a heart rate, a rate of breathing, a blood pressure, a blood flow, or a size of breath of said patient; and using said information in said detecting of the first, second and third different body positions of said patient.

8. The method according to claim 1, further comprising the steps of:

determining a morphology of said sensed activity level signal;

comparing the morphology with a reference morphology; and detecting that said patient is walking if said sensed morphology and said reference morphology shows a correspondence within predetermined terms of reference.

9. The method according to claim 1, further comprising the steps of:

determining a frequency of said sensed activity level signal;

comparing the sensed frequency with a reference frequency; and detecting that said patient is walking if a difference between said sensed frequency and said reference frequency is determined to be within a predetermined frequency range.

10. The method according to claim 9, comprising pre-storing the reference frequency in said medical device.

11. The method according to claim 9, comprising:

obtaining the reference frequency during a training session including the steps of:

determining a morphology and/or frequency of a sensed activity level signal when said patient is walking; and storing said determined morphology and/or frequency of the sensed activity level signal when said patient is walking as a reference morphology and/or a reference frequency, respectively.

12. The method according to claim 1, wherein the step of sensing a trans-thoracic impedance comprises the steps of:

applying an excitation current pulse between a first electrode arranged to be positioned within a heart of the patient and a case of said device; and sensing a voltage between a second electrode arranged to be positioned within a heart of the patient and said case.

13. The method according to claim 12, comprising arranging said first and second electrodes in a lead connectable to said device configured to be located in a right ventricle, in a right atrium, or in a left ventricle of said patient.

14. The method according to claim 1, further comprising the steps of:

calculating each impedance value as a mean value of impedance values obtained during a predetermined period of time; and determining said relation between respective impedance values at said at least two positions using said calculated impedance values.

15. The method according to claim 1, further comprising the step of:

calculating each relation between impedance values as a mean value of relations obtained during a predetermined period of time.

16. The method according to claim 1, further comprising the step of:

communicating said relation and/or said assessed degree of pulmonary edema to an external device on a continuous basis or at regular intervals.

17. The method according to claim 16, further comprising communicating the relation and/or said assessed degree of pulmonary edema via telemetry or trans-telephonically to a location outside of said implantable medical device.

18. An implantable medical device for assessing a degree of pulmonary edema of a patient, said device being connectable to the patient in at least one electrode configuration, comprising:
an impedance sensor that senses a trans-thoracic impedance of said patient via said at least one electrode configuration;
position information obtaining circuit that obtains information related to body positions of said patient;
a value obtaining circuit that obtains impedance values from said impedance signals;
a processing unit configured to:
determine when said patient is in each of a first position, a second position and a third position using said position information, the first body position being an upright position and the second body position and the third body position being a respective one of lying on the back, on the stomach, or on a side;
trigger said impedance sensor to initiate a sensing session in order to sense trans-thoracic impedance signals when said patient is in each of said first body position, said second body position and said third body position; and
determine a relation among first, second and third respective impedance values obtained from respective first, second and third impedance signals; and
a storage unit in which said processing unit stores said relation;
wherein said processing unit is configured to use said relation as a metric of pulmonary edema to emit an output indicating the degree of pulmonary edema
wherein said position information obtaining circuit comprises an activity level sensor that senses an activity level signal of said patient;
wherein said processing unit is configured to use said sensed activity level signal to detect said body positions of said patient and said processing unit is configured to:
determine whether said sensed activity level signal is below a predetermined activity level signal limit; and
detect that the patient is lying down when said sensed activity level signal has been below said signal limit during a predetermined period of time;
wherein said value obtaining circuit obtains AC impedance values from said impedance signals, said processing unit is configured to create an AC impedance morphology using said AC impedance values and is configured to detect whether the patient is lying on the back, on the stomach, or on a side using a AC impedance morphology.

19. The device according to claim 18, wherein said processing unit is configured to determine the variability of the first, second and third impedance values, as said relation.

20. The device according to claim 18, wherein said processing unit is configured to compare a current relation with at least one preceding relation to determine a difference between said current relation and said at least one preceding relation; and wherein said difference is output as said metric.

21. The device according to claim 18, wherein the processing unit is adapted to:
compare a current relation with at least one reference relation value to determine a difference between said current relation and said at least one reference relation; and
use said difference to assess the degree of pulmonary edema.

22. The device according to claim 18, wherein said obtaining means comprises a low pass filter adapted to filter off the AC component of said impedance to obtain impedance values containing substantially only a DC component.

23. The device according to claim 18, wherein said processing unit is configured to, when one of said first, second and third body positions is sensed, delay the initiating of the impedance sensing session a predetermined period of time sufficient to allow the interstitial and/or pulmonary fluid to redistribute in the body.

24. The device according to claim 18, further comprising:
a further sensor selected from the groups consisting of a heart rate sensor, a breath rate sensor, a blood pressure sensor, a blood flow sensor, and a sensor for sensing a size of a breath by said patient; and
wherein said processing unit is configured to use information from said further sensor in detecting said body positions of said patient.

25. The device according to claim 18, wherein said processing unit is configured to:
determine a morphology of said sensed activity level signal;
compare the sensed morphology with a reference morphology; and
detect that said patient is walking if said sensed morphology and said reference morphology shows a correspondence within predetermined terms of reference.

26. The device according to claim 18, wherein said processing unit is adapted to:
determine a frequency of said sensed activity level signal;
compare the sensed frequency with a reference frequency; and
detect that said patient is walking if a difference between said sensed frequency and said reference frequency is determined to be within a predetermined frequency range.

27. The device according to claim 25, comprising a memory in said implantable medical device wherein the reference morphology is pre-stored.

28. The device according to claim 25, wherein said processing unit is configured to:
determine a morphology of a sensed activity level signal in a training session when said patient is walking; and
store said determined morphology of the sensed activity level signal when said patient is walking as a reference morphology, in said storage unit.

29. The device according to claim 18, further comprising:
a current section for applying an excitation current pulse between a first electrode positioned within a heart of the patient and a case of said device; and
a sensing circuit for sensing a voltage between a second electrode arranged to be positioned within a heart of the patient and said case.

30. The device according to claim 29, comprising a lead carrying said first and second electrodes, said lead being connectable to said device and being configured to be located at a site selected from the group consisting of in a right ventricle, in a right atrium, and in a left ventricle of said patient.

31. The device according to claim 18, wherein said processing unit is adapted to:

calculate each impedance value as a mean value of impedance values obtained during a predetermined period of time; and determine said relation between respective impedance values using said calculated impedance values.

32. The device according to claim 18, wherein said processing unit is configured to:

calculate each relation between impedance values as a mean value of relations obtained during a predetermined period of time.

33. The device according to claim 18, further comprising a communication unit that communicates said relation and/or said degree of pulmonary edema to an external device on a continuous basis or at regular intervals.

34. The device according to claim 33, wherein said communication unit communicates said relation and/or said assessed degree of pulmonary edema via telemetry or transtelephonically.

* * * * *